(12) United States Patent
Windfeld

(10) Patent No.: US 11,464,759 B2
(45) Date of Patent: Oct. 11, 2022

(54) 5-HT6 RECEPTOR ANTAGONISTS FOR USE IN THE TREATMENT OF ALZHEIMER'S DISEASE IN PATIENT SUBPOPULATION CARRYING APOE4 ALLELES

(71) Applicant: H. Lundbeck A/S, Valby (DK)

(72) Inventor: Kristian Windfeld, Valby (DK)

(73) Assignee: H. Lundbeck A/S, Valby (DK)

(*) Notice: Subject to any disclaimer, the term of this patent is extended or adjusted under 35 U.S.C. 154(b) by 196 days.

(21) Appl. No.: 15/987,449

(22) Filed: May 23, 2018

(65) Prior Publication Data
US 2018/0353477 A1 Dec. 13, 2018

(30) Foreign Application Priority Data

May 24, 2017 (DK) .............................. PA201700313
Sep. 29, 2017 (DK) .............................. PA201700538

(51) Int. Cl.
| | | |
|---|---|---|
| A61K 31/4045 | (2006.01) | |
| A61K 31/27 | (2006.01) | |
| A61K 31/445 | (2006.01) | |
| A61K 31/55 | (2006.01) | |
| A61P 25/28 | (2006.01) | |
| A61K 45/06 | (2006.01) | |
| A61K 31/496 | (2006.01) | |
| A61K 31/505 | (2006.01) | |

(52) U.S. Cl.
CPC .......... *A61K 31/4045* (2013.01); *A61K 31/27* (2013.01); *A61K 31/445* (2013.01); *A61K 31/496* (2013.01); *A61K 31/505* (2013.01); *A61K 31/55* (2013.01); *A61K 45/06* (2013.01); *A61P 25/28* (2018.01)

(58) Field of Classification Search
CPC ................................................. A61K 31/4045
See application file for complete search history.

(56) References Cited

FOREIGN PATENT DOCUMENTS

| | | | |
|---|---|---|---|
| EP | 2248815 | A2 | 11/2010 |
| RU | 2469723 | C2 | 12/2012 |
| RU | 2569056 | C2 | 11/2015 |
| WO | WO-2004/015140 | A1 | 2/2004 |
| WO | WO-2009/074607 | A1 | 6/2009 |
| WO | WO-2009/093206 | A2 | 7/2009 |
| WO | WO2014037532 | * | 3/2014 |
| WO | WO-2014/165701 | A1 | 10/2014 |
| WO | WO-2016/179569 | A1 | 11/2016 |
| WO | WO-2017/186686 | A1 | 11/2017 |
| WO | WO-2017/194496 | A1 | 11/2017 |

OTHER PUBLICATIONS

Waring et al. (Journal of Alzheimer's Disease, (2015), vol. 47, pp. 137-148) (Year: 2015).*
Knowles et al. Core Evidence (2006), vol. 1, pp. 195-219. (Year: 2006).*
PA201700313, May 24, 2017.*
NCT01955161, Sep. 23, 2016, available at https://www.clinicaltrials.gov/ct2/history/NCT01955161?V_10=View#StudyPageTop.*
NCT02006654, Mar. 31, 2017, available at https://www.clinicaltrials.gov/ct2/history/NCT02006654?V_11=View#StudyPageTop.*
Abushakra et al., Clinical Benefits of Tramiprosate in Alzheimer's Disease Are Associated with Higher Number of APOE4 Alleles: The "APOE4 Gene-Dose Effect", J Prev Alzheimers Dis, 2016;3(4):219-228.*
Altri et al., JAMA 2018, 319 (2): 130-142.*
Abushakra, S., et al., "Clinical Benefits of Tramiprosate in Alzheimer's Disease Are Associated with Higher Number of APOE4 Alleles: The 'APOE4 Gene-Dose Effect,'" J. Prev. Alz. Dis., vol. 3, No. 4, pp. 219-228 (Sep. 2016).
Arnt, J., et al., "Lu AE58054, a 5-HT6 antagonist, reverses cognitive impairment induced by subchronic phencyclidine in a novel object recognition test in rats," Int. J. Neuropsychopharmacol., vol. 13, pp. 1021-1033 (online Jun. 23, 2010).
Berge, S. M., et al., "Pharmaceutical Salts," J. Pharm. Sci., vol. 66, No. 1, pp. 1-19 (Jan. 1977).
Cummings, J. L., et al., "The Neuropsychiatric Inventory: Comprehensive assessment of psychopathology in dementia," Neurology, vol. 44, pp. 2308-2314 (Dec. 1994).
Folstein, M. F., et al., "'Mini-Mental State': A Practical Method for Grading the Cognitive State of Patients for the Clinician," Journal of Psychiatric Research, vol. 12, pp. 189-198 (1975).
Galasko, D., et al., "An Inventory to Assess Activities of Daily Living for Clinical Trials in Alzheimer's Disease," Alzheimer. Dis. Assoc. Disord., vol. 11, Suppl. 2, pp. S33-S39 (1997).
Holtzman, D. M., et al., "Apolipoprotein E and Apolipoprotein E Receptors: Normal Biology and Roles in Alzheimer Disease," published by Cold Spring Harb. Perspect. Med., vol. 2, a006312, pp. 1-23, 24 total pages (online Jan. 10, 2012).
Olanow, C. W., et al., "Continuous intrajejunal infusion of levodopa-carbidopa intestinal gel for patients with advanced Parkinson's disease: a randomised, controlled, double-blind, double-dummy study," Lancet Neurol., vol. 13, pp. 141-149 (online Dec. 20, 2013).
Rosen, W. G., et al., "A New Rating Scale for Alzheimer's Disease," Am. J. Psychiatry, vol. 141, No. 11, pp. 1356-1364 (Nov. 1984).
Roses, A., "Apolipoprotein E Alleles as Risk Factors in Alzheimer's disease," Ann. Rev. Med., vol. 47, pp. 387-400, including table of contents—17 total pages (1996).
International Search Report and Written Opinion dated Aug. 1, 2018 by European Patent Office as International Searching Authority in PCT/EP2018/063402 (20 total pages).

(Continued)

*Primary Examiner* — Svetlana M Ivanova
(74) *Attorney, Agent, or Firm* — Wilmer Cutler Pickering Hale and Dorr LLP

(57) ABSTRACT

The present invention relates to 5-HT$_6$ receptor antagonists for the treatment of Alzheimer's disease where the Alzheimer's disease patient carries one or two ApoE4 alleles comprising administering an effective dose of a 5-HT$_6$ receptor antagonist to improve or augment the effect of an acetylcholinesterase inhibitor.

20 Claims, No Drawings

(56) References Cited

OTHER PUBLICATIONS

Godyn, J., et al., "Therapeutic strategies for Alzheimer's disease in clinical trials," Pharmacological Reports, vol. 68, pp. 127-138 (online Aug. 5, 2015).
Roberts, P. D., et al., "Simulations of symptomatic treatments for Alzheimer's disease: computational analysis of pathology and mechanisms of drug action," Alzheimer's Research & Therapy, vol. 4, No. 50, pp. 1-21 (2012).
Atri, A., et al., "Effect of Idalopirdine as Adjunct to Cholinesterase Inhibitors on Change in Cognition in Patients with Alzheimer Disease," JAMA, vol. 319, No. 2, pp. 1-23 (online Jan. 9, 2018).
Reitz, "Toward Precision Medicine in Alzheimer's Disease," Annals of Translational Medicine, vol. 4 No. 6:107, pp. 1-7 (Mar. 2016) (7 pages).
Wilkinson, et al., "Safety and Efficacy of Idalopirdine, a 5-HT$_6$ Receptor Antagonist, in Patients with Moderate Alzheimer's Disease (LADDER): A Randomized, Double-Blind, Placebo-Controlled Phase 2 Trial," Lancet Neurology, vol. 13, pp. 1092-1099 (online Oct. 6, 2014) (8 pages).
Kucinski et al., "Reducing falls in Parkinson's disease: interactions between donepezil and the 5-HT6 receptor antagonist idalopirdine on falls in a rat model of impaired cognitive control of complex movements," European Journal of Neuroscience (2017), vol. 45(2), pp. 217-231, published online Aug. 18, 2016.
Mashkovsky, M.D., "Medicines," Pharmaceutical Preparations, 16th edition (2012), revised and updated by Novaya Volna, 1216 pages, see pp. 8 and 12-13. English translation included. 13 pages.
Office Action dated Aug. 23, 2021, in Russian patent application No. 2019135609. English translation included. 15 pages.
Brauser, "Two More Phase 3 Trials of Alzheimer's Drug Idalopirdine Fail," Medscape, Feb. 10, 2017. 2 pages. (https://web.archive.org/web/20170211144315/https://www.medscape.com/viewarticle/875632).
H. Lundbeck A/S Corporate Release, "Headline conclusions from the first out of three phase III studies on idalopirdine in Alzheimer's disease," Corporate Release No. 600, pp. 1-3. Sep. 22, 2016.
Taylor, "Lundbeck calls time on Alzheimer's drug after more failures," Fierce Biotech, Feb. 8, 2017. 2 pages. (https://www.fiercebiotech.com/biotech/lundbeck-calls-time-alzheimer-s-drug-after-more-failure).

\* cited by examiner

5-HT6 RECEPTOR ANTAGONISTS FOR USE IN THE TREATMENT OF ALZHEIMER'S DISEASE IN PATIENT SUBPOPULATION CARRYING APOE4 ALLELES

This application claims the benefit of and priority to Danish Patent Application No. PA201700313, filed May 24, 2017, and Danish Patent Application No. PA201700538, filed Sep. 29, 2017, each of which is incorporated by reference in its entirety for all purposes.

FIELD OF THE INVENTION

The present invention relates to 5-HT$_6$ receptor antagonists and pharmaceutically acceptable salts thereof for use in the treatment of Alzheimer's disease, wherein the treatment further comprising the use of an acetylcholinesterase inhibitor, and the Alzheimer's disease patient carries one or two ApoE4 alleles

BACKGROUND OF THE INVENTION

Dementia is a clinical syndrome characterized by deficits in multiple areas of cognition that cannot be explained by normal aging, a noticeable decline in function, and an absence of delirium. In addition, neuropsychiatric symptoms are often present already at first diagnosis and then increase in numbers and intensity over time as the disease progresses. The ε4 allele of the apolipoprotein E gene (APOE4) is known to be one of the most important genetic risk factors for Alzheimer's disease (AD) (Roses A. Apolipoprotein E alleles as risk factors in Alzheimer's disease. Ann Rev Med. 1996; 47; 387-400; the contents of which are hereby incorporated by reference). The increased risk is thought to be associated with the APOE4 isoform showing reduced clearance of Aβ peptides and promoting their aggregation (Holzman D M et al. Apolipoprotein E and apolipoprotein E receptors: normal biology and roles in Alzheimer disease. Cold Spring Harb Perspect Med. 2012; 2:a006312; the contents of which are hereby incorporated by reference).

A phase III program using tramiprosate, a GABA receptor modulator, as a disease modifier in the treatment of AD was reported not to meet its primary endpoint, but a prespecified subgroup analysis suggested potential efficacy in apolipoprotein E4 carriers (Abushakra, S. Clinical Benefits of Tramiprosate in Alzheimer's disease Are Associated with Higher Number of APOE4 Alleles: The "APOE4 Gene-Dose Effect. J Prev Alz Dis 2016; 3(4):219-228; the contents of which are hereby incorporated by reference).

The use of selective 5-HT$_6$ receptor antagonists to treat cognitive dysfunction has been suggested and is based on several lines of reasoning. For example, selective 5-HT$_6$ receptor antagonists have been shown to modulate cholinergic and glutamatergic neuronal function.

N-(2-(6-fluoro-1H-indol-3-yl)-ethyl)-3-(2,2,3,3-tetrafluoropropoxy)-benzylamine, INN-name idalopirdine, is a potent and selective 5-HT$_6$ receptor antagonist which is currently in clinical development. N-(2-(6-fluoro-1H-indol-3-yl)-ethyl)-3-(2,2,3,3-tetrafluoropropoxy)-benzylamine has also been disclosed as Lu AE58054.

N-(2-(6-fluoro-1H-indol-3-yl)-ethyl)-3-(2,2,3,3-tetrafluoropropoxy)-benzylamine was first disclosed in WO 02/078693 (the contents of which are hereby incorporated by reference) and a dose range for N-(2-(6-fluoro-1H-indol-3-yl)-ethyl)-3-(2,2,3,3-tetrafluoropropoxy)-benzylamine was proposed in WO 2014/037532, the contents of which are hereby incorporated by reference.

A randomised, double-blind, placebo-controlled phase II trial has been reported in *Lancet Neurol* 2014; 13:1092-99 (published online Oct. 6, 2014; hereinafter referred to as the LADDER study; the contents of which are hereby incorporated by reference). The LADDER study was conducted in patients with moderate AD (MMSE 12-19), using idalopirdine 90 mg/day (30 mg TID) added to stable donepezil. The LADDER study produced significant improvement in cognitive performance relative to donepezil monotherapy.

A subsequent phase III program consisting of three 24-week studies (ClinicalTrials.gov Identifier: NCT01955161; NCT02006641; NCT02006654; the contents of which are hereby incorporated by reference) of idalopirdine as an adjunctive treatment to acetylcholinesterase inhibitor in patients with mild-moderate Alzheimer's disease (MMSE 12-22) with a fixed dose of idalopirdine (10, 30, and 60 mg QD) did not replicate the phase II efficacy results.

Avineuro Pharmaceuticals is developing an oral small-molecule 5-HT$_6$ receptor antagonist, AVN-211 (CD-008-0173), for the potential treatment of the cognitive symptoms as well as for Alzheimer's disease. AVN-211 is a 3-sulfonyl-pyrazolo[1,5-a]pyrimidine derivative and is disclosed in WO 2009/093206 (the contents of which are hereby incorporated by reference) as 3-Benzenesulfonyl-5,7-dimethyl-2-methylsulfanyl-pyrazolo[1,5-a]pyrimidine.

Axovant Sciences Ltd is developing an oral small-molecule 5-HT$_6$ receptor antagonist interpirdine (RVT-101/SB-742457, CAS Registry Number 607742-69-8) for the potential treatment of Alzheimer's disease. RVT-101 is an 8-piperazin-1-yl quinoline derivative and is disclosed in WO 2009/074607 (the contents of which are hereby incorporated by reference) as 3-phenylsulfonyl-8-piperazin-1-yl-quinoline.

Presently, there is no cure and no treatment that slows or stops the progression of dementia. There is a need for improved drug treatments that improve the quality of life of patients suffering from the symptoms of Alzheimer's Disease.

SUMMARY OF THE INVENTION

The present provides a treatment of Alzheimer's disease with a 5-HT$_6$ receptor antagonist as an adjunctive therapy to acetylcholinesterase inhibitors in an Alzheimer's disease patient subpopulation group, wherein the patients carry either one APOE4 allele (heterozygous) or two APOE4 alleles (homozygous), said therapy comprising administering an effective dose of a 5-HT$_6$ receptor antagonist to improve or augment the effect of the treatment with an acetylcholinesterase inhibitor, particularly on cognitive performance.

DETAILED DESCRIPTION OF THE INVENTION

The inventors of the present invention have surprisingly found that whereas idalopirdine as adjunctive treatment to acetylcholinesterase inhibitors in patients with mild-moderate Alzheimer's disease produced no significant improvement in cognitive performance relative to donepezil monotherapy, a significant improvement in cognitive performance relative to donepezil monotherapy was achieved with idalopirdine as adjunctive treatment to donepezil in APOE4 homozygote patients and APOE4 heterozygote patients with mild-moderate Alzheimer's disease (MMSE 12-22).

Since idalopirdine is a 5-HT$_6$ receptor antagonist with high specificity and virtually no binding to other pharmacological receptors, it is reasonable to surmise that observed enhanced activity is due to its 5-HT$_6$ receptor antagonist activity and therefore a general property of 5-HT$_6$ receptor antagonists. Accordingly, 5-HT$_6$ receptor antagonists such as AVN-211 and RVT-101, are expected to also give rise to an enhanced treatment response in Alzheimer's disease in APOE4/4 homozygote patients and APOE4 heterozygote patients with mild-moderate Alzheimer's disease.

An aspect of the invention is directed to a 5-HT$_6$ receptor antagonist or a pharmaceutically acceptable salt thereof for use in the treatment of Alzheimer's disease, the treatment further comprising the use of an acetylcholinesterase inhibitor, wherein the Alzheimer's disease patient carries one or two ApoE4 alleles.

EMBODIMENTS OF THE INVENTION

In the following, embodiments of the invention are disclosed. The first embodiment is denoted E1, the second embodiment is denoted E2 and so forth.

E1 A 5-HT$_6$ receptor antagonist, or a pharmaceutically acceptable salt thereof, for use in treating Alzheimer's disease, where the Alzheimer's disease patient carries one or two ApoE4 alleles, by improving or augmenting the effect of the treatment with an acetylcholinesterase inhibitor.

E2 In an embodiment of E1, the 5-HT$_6$ receptor antagonist is selected from the group consisting of idalopirdine, AVN-211 and RVT-101 or pharmaceutically acceptable salts of said 5-HT$_6$ receptor antagonists.

E3 In an embodiment of E1 or E2, the 5-HT$_6$ receptor antagonist is idalopirdine or a pharmaceutically acceptable salt thereof.

E4 In an embodiment of E1 or E3, the 5-HT$_6$ receptor antagonist is the hydrochloride salt of idalopirdine.

E5 In an embodiment of E1 or E2, the 5-HT$_6$ receptor antagonist is AVN-211 or a pharmaceutically acceptable salt thereof.

E6 In an embodiment of E1 or E2, the 5-HT$_6$ receptor antagonist is RVT-101 or a pharmaceutically acceptable salt thereof.

E7 In an embodiment of E1, the acetylcholinesterase inhibitor is selected from the group consisting of donepezil, rivastigmine and galantamine or pharmaceutically acceptable salts of said acetylcholinesterase inhibitors.

E8 In an embodiment of E1 or E7, the acetylcholinesterase inhibitor is donepezil or a pharmaceutically acceptable salt thereof.

E9 In an embodiment of E1 or E8, the acetylcholinesterase inhibitor is the hydrochloride salt of donepezil.

E10 In an embodiment of E1 or E7, the acetylcholinesterase inhibitor is rivastigmine or a pharmaceutically acceptable salt thereof.

E11 In an embodiment of E1 or E10, the acetylcholinesterase inhibitor is the hydrochloride salt or the tartrate salt of rivastigmine.

E12 In an embodiment of E1 or E7, the acetylcholinesterase inhibitor is galantamine or a pharmaceutically acceptable salt thereof.

E13 In an embodiment of E1 or E12, the acetylcholinesterase inhibitor is the hydrobromide salt of galantamine.

E14 In an embodiment of E1, E3 or E8, the 5-HT$_6$ receptor antagonist is idalopirdine and the acetylcholinesterase inhibitor is donepezil.

E15 In an embodiment of E1 or E14, the 5-HT$_6$ receptor antagonist is the hydrochloride salt of idalopirdine and the acetylcholinesterase inhibitor is the hydrochloride salt of donepezil.

E16 In an embodiment of E1, E14 or E15 the dosage range of idalopirdine is from 60 mg/day to 120 mg/day.

E17 In an embodiment of E1, E3, E4, E14 or E15 the dosage range of idalopirdine is from 60 mg/day to 90 mg/day.

E18 In an embodiment of E17 the dosage of idalopirdine is 60 mg/day.

E19 In an embodiment of E17 the dosage of idalopirdine is 90 mg/day.

E20 In an embodiment of E1, E8, E9, E14 or E15 the dosage range of donepezil is from 2 mg/day to 25 mg/day, preferably from 5 mg/day to 23 mg/day.

E22 In an embodiment of any the previous embodiments the 5-HT$_6$ receptor antagonist is dosed once daily (QD) or twice daily (BID) to obtain the desired daily dose.

E23 In an embodiment of any of E1, E16, E17, E18 or E19 idalopirdine is dosed BID.

E21 A pharmaceutical composition comprising a 5-HT$_6$ receptor antagonist selected from the group consisting of idalopirdine, RVT-101 and AVN-211, or pharmaceutically acceptable salts of said 5-HT$_6$ receptor antagonists, and an acetylcholinesterase inhibitor selected from the group consisting of donepezil, rivastigmine and galantamine, or pharmaceutically acceptable salts thereof, for the treatment of Alzheimer's disease where the Alzheimer's disease patient carries one or two ApoE4 alleles.

E22 Use of a 5-HT$_6$ receptor antagonist selected from the group consisting of idalopirdine, RVT-101 and AVN-211, or pharmaceutically acceptable salts thereof, for the manufacture of a medicament for the treatment of Alzheimer's disease where the Alzheimer's disease patient carries one or two ApoE4 alleles.

E23 Use of a 5-HT$_6$ receptor antagonist selected from the group consisting of idalopirdine, RVT-101 and AVN-211, or pharmaceutically acceptable salts 5-HT$_6$ receptor antagonist, and an acetylcholinesterase inhibitor selected from the group consisting of donepezil, rivastigmine and galantamine, or pharmaceutically acceptable salts of acetylcholinesterase inhibitors, for the manufacture of a medicament for the treatment of Alzheimer's disease where the Alzheimer's disease patient carries one or two ApoE4 alleles.

E24 In an embodiment of any of the previous embodiments the Alzheimer's disease is at a mild to moderate stage.

E25 In an embodiment of any of the previous embodiments the Alzheimer's disease is at a moderate to severe stage.

E26 A method of treating Alzheimer's disease where the Alzheimer's disease patient carries one or two ApoE4 alleles and wherein the patient is being treated with an acetylcholinesterase inhibitor, the method comprising the further administration a 5-HT$_6$ receptor antagonist or a pharmaceutically acceptable salt thereof.

E27 A dosage regimen for the symptomatic treatment of Alzheimer's disease in a subgroup population of Alzheimer's disease patient carrying one or two ApoE4 alleles comprising the adjunctive use of a 5-HT$_6$ receptor antagonist and an acetylcholinesterase inhibitor.

E28 A 5-HT$_6$ receptor antagonist, or a pharmaceutically acceptable salt thereof, for use in treating Alzheimer's disease in a patient, wherein the patient is also receiving treatment with an acetylcholinesterase inhibitor, and wherein the patient carries one or two ApoE4 alleles.

Definitions

Throughout the specification, the term "5-HT$_6$ receptor antagonist" as well as any specific 5-HT$_6$ receptor antagonist, such as idalopirdine, AVN-211 or RVT-101, is intended to include, unless otherwise specified, any form of the compound, such as the free base and pharmaceutically acceptable salts. The free base and pharmaceutically acceptable salts include anhydrous forms and solvated forms such as hydrates. The anhydrous forms include amorphous and crystalline forms, and the solvates include crystalline forms. Further, unless otherwise specified, the term "5-HT$_6$ receptor antagonist" includes the human 5-HT$_6$ receptor antagonist (which also may be denoted "h5-HT$_6$ receptor antagonist").

Likewise, the term "acetylcholinesterase inhibitor" (abbreviated "AChEI") as well as any specific acetylcholinesterase inhibitor, such as "donepezil", is intended to include any form of the compound, such as the free base and pharmaceutically acceptable salts etc.

The term "acetylcholinesterase inhibitor" (AChEI) is known to those skilled in art and includes compounds selected from the group consisting of donepezil ((RS)-2-[(1-Benzyl-4-piperidyl)methyl]-5,6-dimethoxy-2,3-dihydroinden-1-one), rivastigmine ((S)-3-[1-(dimethylamino)ethyl] phenyl N-ethyl-N-methylcarbamate), and galantamine ((4aS,6R,8aS)-5,6,9,10,11,12-Hexahydro-3-methoxy-11-methyl-4aH-[1]benzofuro[3a,3,2-ef][2]benzazepin-6-ol) and tacrine (1,2,3,4-tetrahydroacridin-9-amine). The AchEIs may be abbreviated as follows: donepezil DON, rivastigmine RIV, and galantamine GAL.

The terms "active pharmaceutical ingredient" and "active ingredient" cover 5-HT$_6$ receptor antagonists and AChEI.

The FDA approved dosages of the acetylcholinesterase inhibitor are encompassed by the instant invention. For example, the dosages of donepezil are shown to be effective in controlled clinical trials of the treatment of mild to moderate Alzheimer's disease are 5 mg or 10 mg administered orally once per day. A 23 mg orally once daily dose of donepezil is also approved for treating moderate to severe AD.

In the present context, when a 5-HT$_6$ receptor antagonist, such as idalopirdine (may be abbreviated IDL), AVN-211 or RVT-101 or any other 5-HT$_6$ receptor antagonist, is used in combination with an AChEI, such as donepezil, rivastigmine, tacrine or galantamine, this indicates in one embodiment that said two compounds can be administrated simultaneously for example in a pharmaceutical composition comprising both compounds. In another embodiment, when a 5-HT$_6$ receptor antagonist is used in combination with an AChEI, this indicates that said two compounds are administered separately in suitable individual pharmaceutical compositions. These individual compositions may be administered simultaneously e.g. with regular intervals once daily either morning or evening, or they may be administered independently e.g. one compound with regular intervals once daily in the morning and the other compound with regular intervals once daily in the evening.

A "therapeutically effective dose" of 5-HT$_6$ receptor antagonist is an amount sufficient to provide an observable therapeutic benefit compared to baseline clinically observable signs and symptoms of Alzheimer's disease as measured by ADAS-cog (Rosen W G et al. A new scale for Alzheimer's disease. *Am J Psychiatry* 1984; 141: 1356-64; the contents of which are hereby incorporated by reference).

ADCS-ADL is measured according to Galasko et al. An inventory to assess activities of daily living for clinical trials in Alzheimer's disease. The Alzheimer's Disease Cooperative Study. *Alzheimer Dis Assoc Disord.* 1997; 11 Suppl 2:S33-9; the contents of which are hereby incorporated by reference.

The term "mild to moderate Alzheimer's disease" shall mean a score between 12 and 22 (both endpoints included) on the mini mental state examination (MMSE) scale.

Neuropsychiatric Inventory (NPI) is measured according to Cummings, J. L., Mega, M., Gray, K., Rosenberg-Thompson, S., Carusi, D. A., & Gornbein, J. The Neuropsychiatric Inventory: comprehensive assessment of psychopathology in dementia. *Neurology* 1994; 44: 2308-2314; the contents of which are hereby incorporated by reference.

Mini Mental State Examination (MMSE) is measured according to Folstein, M. F., Folstein, S. E. & McHugh, P. R. "Mini-mental state": a practical method for grading the cognitive state of patients for the clinician. *Journal of psychiatric research* 1975 12(3): 189-198; the contents of which are hereby incorporated by reference.

Alzheimer's disease patients carrying one mutation in the ε4 apolipoprotein E gene may sometimes be referred to as "APOE4 heterozygote patients"; Alzheimer's disease patients carrying two mutations the ε4 apolipoprotein E gene may sometimes be referred to as "APOE4 homozygote patients" or "APOE4/4 homozygote patients".

The term "daily" means a given, continuous twenty-four (24) hour period.

The term "dose" is used herein to mean administration of 5-HT$_6$ receptor antagonist or acetylcholinesterase inhibitor in one dosage form to the patient being treated. In some embodiments, the dose is a single oral formulation. In some embodiments, the dose is formulated as a tablet, a capsule, a pill, or a patch administered to the patient.

In the present context, a "unit dosage form" refers to a formulation unit of a pharmaceutical composition e.g. a tablet or a capsule.

The term "effective daily dose" means the total amount of 5-HT$_6$ receptor antagonist or AChEI administered to a patient in need of therapy in a continuous, twenty-four (24) hour period. As a non-limiting example used herein solely to illustrate the meaning of the term, an effective daily dose of 90 mg shall mean and include administering a single dose of 90 mg in a twenty four hour period, administering two doses of 45 mg each within a twenty four hour period, and administering three doses of 30 mg each in a twenty four hour period, and so on. When administering 5-HT$_6$ receptor antagonist in such a manner, i.e. more than once in a twenty four hour period, such administrations can be spread evenly through the twenty four hour period or even be administered simultaneously or nearly so.

The term "dose range" as used herein refers to an upper and a lower limit of an acceptable variation of the amount of agent specified. Typically, a dose of the agent in any amount within the specified range can be administered to patients undergoing treatment.

The term "treat" is used herein to mean to relieve, reduce or alleviate at least one symptom of a disease in a subject. For example, in relation to dementia, the term "treat" may mean to relieve or alleviate cognitive impairment (such as impairment of memory and/or orientation) or impairment of global functioning (overall functioning, including activities of daily living) and/or slow down or reverse the progressive deterioration in global or cognitive impairment.

Pharmaceutically Acceptable Salts

The present invention also comprises salts of the 5-HT$_6$ receptor antagonists, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

In a particular embodiment of the present invention 5-HT$_6$ receptor antagonist is in the form of a hydrochloric salt of idalopirdine.

Pharmaceutical Compositions

The present invention further provides a pharmaceutical composition comprising a therapeutically effective amount of a 5-HT$_6$ receptor antagonist and a pharmaceutically acceptable carrier or diluent. The present invention also provides a pharmaceutical composition comprising a therapeutically effective amount of one of the 5-HT$_6$ receptor antagonist and a pharmaceutically acceptable carrier or diluent.

The 5-HT$_6$ receptor antagonist may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22$^{nd}$ Edition, Gennaro, Ed., Mack Publishing Co., Easton, Pa., 2013, the contents of which are hereby incorporated by reference.

The pharmaceutical compositions may be specifically formulated for administration by any suitable route such as oral, rectal, nasal, pulmonary, topical (including buccal and sublingual), transdermal and parenteral (including subcutaneous, intramuscular and intravenous) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain a total amount of active pharmaceutical ingredient or pharmaceutically acceptable salt thereof from about 10 mg to about 200 mg, such as from about 60 mg to about 200 mg.

The 5-HT$_6$ receptor antagonists of this invention are generally utilized as the free substance or as a pharmaceutically acceptable salt thereof. One example is an acid addition salt of a 5-HT$_6$ receptor antagonist which has the same utility as of a free base. When a 5-HT$_6$ receptor antagonist contains a free base, such salts are prepared in a conventional manner by treating a solution or suspension of a free base of the 5-HT$_6$ receptor antagonist with a pharmaceutically acceptable acid. Representative examples of suitable organic and inorganic acids are described above.

For parenteral administration, solutions of the 5-HT$_6$ receptor antagonist in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The 5-HT$_6$ receptor antagonist may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the 5-HT$_6$ receptor antagonist and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

The 5-HT6 receptor antagonist is generally utilized as the free substance or as a pharmaceutically acceptable salt thereof. Examples of suitable organic and inorganic acids are described above.

Dosing Regimen

The dosing regimen for the 5-$HT_6$ antagonist will depend on the actual pharmacokinetic profile of the antagonist, but generally the dose range will be 5-200 mg/day dosed once or twice daily. For idalopirdine the preferred dose range is 10-120 mg/day dosed once or twice daily, preferably once daily. The preferred dose range for idalopirdine is 60-120 mg/day dosed BID or QD.

The dosing regimen for the AChEI will depend on the actual pharmacokinetic profile of the inhibitor, but generally the dose range will be 5-200 mg/day dosed once or twice daily. Galantamine is typically dosed from 8 mg/day to 24 mg/day, rivastigmine is typically dosed from 3 mg/day to 12 mg/day, and donepezil is typically dosed from 5 mg/day to 23 mg/day.

In an embodiment of this aspect of the invention, the treatment involves the use of 60-90 mg/day of idalopirdine or a pharmaceutically acceptable salt thereof and 5-23 mg/day of donepezil or a pharmaceutically acceptable salt thereof. The 5-$HT_6$ antagonist may be administered simultaneously with an AChEI or the 5-$HT_6$ antagonist and the AChEI may be administered independently of each other.

In the case where the 5-$HT_6$ antagonist is administered simultaneously with an AChEI the two compounds may be contained in the same unit dosage form (e.g. a single tablet comprising both the 5-$HT_6$ receptor antagonist and an AChEI) or in separate unit dosage forms (e.g. two tablets comprising the 5-$HT_6$ receptor antagonist and an AChEI respectively). Accordingly an aspect of the invention is directed to a pharmaceutical composition comprising 60-90 mg of idalopirdine or a pharmaceutically acceptable salt thereof and 5-23 mg of donepezil or a pharmaceutically acceptable salt thereof, such as comprising 60, 65, 70, 75, 80, 85 or 90 mg of idalopirdine or a pharmaceutically acceptable salt thereof and 5, 7.5, 10, 15, 20 or 23 mg of donepezil or a pharmaceutically acceptable salt thereof. Alternatively, a pharmaceutical composition comprising 30-50 mg of idalopirdine or a pharmaceutically acceptable salt thereof and 2-15 mg of donepezil or a pharmaceutically acceptable salt thereof, such as comprising 30, 25, 40, 45 or 50 mg of idalopirdine or a pharmaceutically acceptable salt thereof and comprising 2, 2.5, 3, 5, 10, 12, or 15 mg of donepezil or a pharmaceutically acceptable salt thereof. Another aspect of the invention is directed to a pharmaceutical composition comprising 60-90 mg of idalopirdine or a pharmaceutically acceptable salt thereof and 8-24 mg of galantamine or a pharmaceutically acceptable salt thereof, such as comprising 60, 65, 70, 75, 80, 85 or 90 mg of idalopirdine or a pharmaceutically acceptable salt thereof and 8, 9, 10, 15, 20 or 24 mg of galantamine or a pharmaceutically acceptable salt thereof. Yet another aspect of the invention is directed to a pharmaceutical composition comprising 60-90 mg of idalopirdine or a pharmaceutically acceptable salt thereof and 3-12 mg of rivastigmine or a pharmaceutically acceptable salt thereof, such as comprising 60, 65, 70, 75, 80, 85 or 90 mg of idalopirdine or a pharmaceutically acceptable salt thereof and 3, 4, 5, 6, 7, 8, 9, 10, 11, of 12 mg of rivastigmine or a pharmaceutically acceptable salt thereof.

Unless otherwise specified the dose is calculated on the basis of the free base of the active pharmaceutical ingredient.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The use of the terms "a" and "an" and "the" in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

EXPERIMENTAL

Example 1: Binding Affinity of Idalopirdine, Assay and Results

Previously 5-HT binding affinity of idalopirdine was determined as described in Arnt J, et al. Lu AE58054, a 5-$HT_6$ receptor antagonist, reverses cognitive impairment induced by subchronic phencyclidine in a novel object recognition test in rats. *Int J Neuropsychopharmacol* 2010; 13: 1021-1033; the contents of which are hereby incorporated by reference. The reported results show that N-(2-(6-fluoro-1H-indol-3-yl)-ethyl)-3-(2,2,3,3-tetrafluoro-propoxy)-benzylamine is a potent and selective human 5-HT$_6$ receptor antagonist with the following affinity for human 5-HT$_6$ receptor and other human 5-HT receptor subtypes:

TABLE 1

Inhibition of 5-HT receptors by idalopirdine

| Receptor | K$_i$ (nM) |
|---|---|
| h5-HT$_6$ | 0.83 |
| h5-HT$_{1A}$ | 2300 |
| h5-HT$_{1B}$ | >10,000 |
| h5-HT$_{1D}$ | 2600 |
| h5-HT$_{1E}$ | >4600 |
| h5-HT$_{1F}$ | 2400 |
| h5-HT$_{2A}$ | 83 |
| h5-HT$_{2B}$ | >4100 |
| h5-HT$_{2C}$ | 250 |
| h5-HT$_7$ | >10,000 |

Example 2: The Phase III Studies

The phase III program was sponsored by H. Lundbeck A/S (HLu) and consisted of three 24-week, double-blind, parallel group, placebo-controlled, fixed-dose (10, 30, and 60 mg QD) studies of idalopirdine as adjunctive treatment to AChEIs in patients aged 50 years or more with mild-moderate AD (MMSE 12-22 at screening):

TABLE 2

Phase III studies

| Clinical trials identifier | HLu identifier | Idalopirdine dosage (mg/QD) | Acetylcholinesterase inhibitor |
|---|---|---|---|
| NCT01956151 | 14861A | 30 or 60 | Donepezil |
| NCT02006641 | 14862A | 10 or 30 | Donepezil |
| NCT02006654 | 14863A | 60 | Donepezil, rivastigmine, galantamine |

The primary endpoint was change from baseline to Week 24 in Alzheimer's disease Assessment Scale-cognitive subscale (ADAS-cog). This end-point addresses the primary objective of the study, which was to establish efficacy of idalopirdine as adjunctive therapy to donepezil for symptomatic treatment of patients with mild-moderate AD.

The key secondary endpoints included a change from baseline to Week 24 in Alzheimer's disease Cooperative Study-Activities of Daily Living Inventory (ADCS-ADL) total score.

Mine Mental State Examination (MMSE) was included as a secondary endpoint supportive of the primary objective.

Neuropsychiatric Inventory (NPI) was included as an endpoint supportive of the secondary objective.

Example 3: Treatment Effect of Idalopirdine on ADAS-Cog, ADCS-ADL, MMSE and NPI in APOE4 Heterozygous or Homozygous AD Patients In the tables below a negative effect value for ADAS-cog and NPI reflects a positive treatment effect, while for ADL and MMSE a positive effect value reflects a positive treatment effect:

TABLE 3

14861A 60 mg versus placebo

| Endpoint | Number of ApoE4 alleles | Effect of 60 mg IDL | 95% CI Lower | 95% CI Upper | P-value |
|---|---|---|---|---|---|
| Change in ADAS-cog at week 24 | 0 | 1.14 | −0.33 | 2.62 | 0.1281 |
|  | 1 | −0.67 | −2.03 | 0.69 | 0.3323 |
|  | 2 | −1.87 | −4.68 | 0.94 | 0.1909 |
|  | 2 vs 0 | −3.02 | −6.19 | 0.16 | 0.0623 |
|  | (1 or 2) vs 0 | −2.42 | −4.56 | −0.27 | 0.0275 |
| Change in ADCS-ADL at week 24 | 0 | −1.29 | −3.35 | 0.77 | 0.2198 |
|  | 1 | 0.75 | −1.14 | 2.64 | 0.4371 |
|  | 2 | 2.06 | −1.86 | 5.98 | 0.3021 |
|  | 2 vs 0 | 3.35 | −1.08 | 7.78 | 0.1379 |
|  | (1 or 2) vs 0 | 2.69 | −0.30 | 5.69 | 0.0781 |
| Change in MMSE at week 24 | 0 | −0.68 | −1.32 | −0.05 | 0.0346 |
|  | 1 | 0.64 | 0.06 | 1.22 | 0.0294 |
|  | 2 | 1.11 | −0.07 | 2.28 | 0.0649 |
|  | 2 vs 0 | 1.79 | 0.45 | 3.13 | 0.0087 |
|  | (1 or 2) vs 0 | 1.56 | 0.65 | 2.47 | 0.0008 |
| Change in NPI at week 24 | 0 | 0.96 | −1.69 | 3.61 | 0.4787 |
|  | 1 | −0.43 | −2.87 | 2.00 | 0.7279 |
|  | 2 | −4.52 | −9.58 | 0.54 | 0.0797 |
|  | 2 vs 0 | −5.48 | −11.2 | 0.23 | 0.0600 |
|  | (1 or 2) vs 0 | −3.44 | −7.30 | 0.43 | 0.0813 |

Results presented in Table 3 show a better effect of 60 mg QD as an adjunctive treatment to idalopirdine in AD patients carrying one or two ApoE4 alleles for both ADAS-cog and ADCS-ADL as well as for MMSE and NPI compared to AD patients without ApoE4 alleles in the 14861A study. The interaction effect between ApoE4 carrier status and treatment with 60 mg idalopirdine is significant for ADAS-cog when comparing the effect in those with 1 or 2 alleles to those with 0 (p=0.0275).

TABLE 4

Results for 14863A 60 mg versus placebo

| Endpoint | Number of ApoE4 alleles | Effect of 60 mg IDL | 95% CI Lower | 95% CI Upper | P-value |
|---|---|---|---|---|---|
| Change in ADAS-cog at week 24 | 0 | −0.75 | −2.13 | 0.63 | 0.2885 |
| | 1 | −0.18 | −1.60 | 1.24 | 0.8005 |
| | 2 | −2.23 | −4.78 | 0.32 | 0.0869 |
| | 2 vs 0 | −1.48 | −4.39 | 1.43 | 0.3176 |
| | (1 or 2) vs 0 | −0.46 | −2.47 | 1.56 | 0.6554 |
| Change in ADCS-ADL at week 24 | 0 | 0.50 | −1.34 | 2.33 | 0.5953 |
| | 1 | 0.83 | −1.05 | 2.71 | 0.3871 |
| | 2 | 1.86 | −1.52 | 5.25 | 0.2804 |
| | 2 vs 0 | 1.37 | −2.49 | 5.22 | 0.4868 |
| | (1 or 2) vs 0 | 0.85 | −1.82 | 3.52 | 0.5325 |
| Change in MMSE at week 24 | 0 | 0.16 | −0.49 | 0.81 | 0.6282 |
| | 1 | 0.42 | −0.25 | 1.09 | 0.2184 |
| | 2 | 0.96 | −0.24 | 2.16 | 0.1157 |
| | 2 vs 0 | 0.80 | −0.57 | 2.17 | 0.2520 |
| | (1 or 2) vs 0 | 0.53 | −0.42 | 1.48 | 0.2755 |
| Change in NPI at week 24 | 0 | −0.09 | −2.14 | 1.96 | 0.9306 |
| | 1 | 0.34 | −1.77 | 2.45 | 0.7514 |
| | 2 | −2.06 | −5.86 | 1.74 | 0.2867 |
| | 2 vs 0 | −1.97 | −6.29 | 2.35 | 0.3711 |
| | (1 or 2) vs 0 | −0.77 | −3.76 | 2.22 | 0.6136 |

Table 4 shows that the trend towards better effect of 60 mg QD as an adjunctive treatment to idalopirdine in AD patients carrying one or two ApoE4 alleles also is apparent in the 14863A study although the interaction is not statistically significant in this study alone.

TABLE 5

Results for 14861A and 14863A pooled 60 mg versus placebo

| Endpoint | Number of ApoE4 alleles | Effect of 60 mg IDL | 95% CI Lower | 95% CI Upper | P-value |
|---|---|---|---|---|---|
| Change in ADAS-cog at week 24 | 0 | 0.02 | −0.99 | 1.02 | 0.9757 |
| | 1 | −0.41 | −1.39 | 0.57 | 0.4134 |
| | 2 | −2.11 | −3.99 | −0.23 | 0.0277 |
| | 2 vs 0 | −2.13 | −4.26 | 0.01 | 0.0507 |
| | (1 or 2) vs 0 | −1.28 | −2.74 | 0.19 | 0.0872 |
| Change in ADCS-ADL at week 24 | 0 | −0.21 | −1.57 | 1.16 | 0.7685 |
| | 1 | 0.77 | −0.56 | 2.11 | 0.2565 |
| | 2 | 1.88 | −0.68 | 4.44 | 0.1492 |
| | 2 vs 0 | 2.09 | −0.81 | 4.98 | 0.1586 |
| | (1 or 2) vs 0 | 1.53 | −0.46 | 3.52 | 0.1311 |
| Change in MMSE at week 24 | 0 | −0.20 | −0.65 | 0.26 | 0.3952 |
| | 1 | 0.53 | 0.09 | 0.97 | 0.0175 |
| | 2 | 1.00 | 0.18 | 1.83 | 0.0175 |
| | 2 vs 0 | 1.20 | 0.26 | 2.14 | 0.0128 |
| | (1 or 2) vs 0 | 0.96 | 0.31 | 1.61 | 0.0038 |
| Change in NPI at week 24 | 0 | 0.35 | −1.32 | 2.02 | 0.6810 |
| | 1 | −0.04 | −1.67 | 1.58 | 0.9579 |
| | 2 | −3.06 | −6.18 | 0.07 | 0.0550 |
| | 2 vs 0 | −3.41 | −6.95 | 0.14 | 0.0594 |
| | (1 or 2) vs 0 | −1.90 | −4.33 | 0.53 | 0.1248 |

The pooled estimates based on studies 14861A and 14863A (Table 5) suggest an increased efficacy of idalopirdine 60 mg with increase in number of ApoE4 alleles.

The effect on ADAS-cog is significant with 2 alleles (p=0.0277) and the interaction contrasting those with 2 alleles to those with 0 alleles is borderline significant (p=0.052).

The estimates for ADCS-ADL are consistent with the pattern seen for ADAS-cog with more functional improvement associated with more ApoE4 alleles although the effects are not statistically significant.

The effect of idalopirdine on MMSE is significant with both 1 and 2 ApoE4 alleles.

The effect on NPI is borderline significant with 2 ApoE4 alleles (p=0.0550) and likewise is the interaction contrasting those with 2 ApoE4 alleles to those with 0 alleles borderline significant (p=0.0594).

The invention claimed is:

1. A method of treating Alzheimer's disease in a subject in need thereof comprising administering idalopirdine or a pharmaceutically acceptable salt thereof, in a dose of 60-120 mg per day; wherein the subject carries one or two APOE4 alleles; and wherein the subject is being treated with an acetylcholinesterase inhibitor or a pharmaceutically acceptable salt thereof, in a dose of 3-24 mg per day.

2. The method of claim 1, wherein the acetylcholinesterase inhibitor is selected from the group consisting of donepezil or a pharmaceutically acceptable salt thereof, in a dose of 5-23 mg per day; rivastigmine or a pharmaceutically acceptable salt thereof, in a dose of 3-12 mg per day; and galantamine or a pharmaceutically acceptable salt thereof, in a dose of 8-24 mg per day.

3. The method of claim 2, wherein the acetylcholinesterase inhibitor is donepezil or a pharmaceutically acceptable salt thereof, in a dose of 5-23 mg per day.

4. The method of claim 1, wherein idalopirdine or a pharmaceutically acceptable salt thereof is administered in a dose of 60-90 mg per day.

5. The method of claim 4, wherein idalopirdine or a pharmaceutically acceptable salt thereof is administered in a dose of 60 mg per day.

6. The method of claim 1, wherein idalopirdine or a pharmaceutically acceptable salt thereof is administered in a dose of 60 mg per day; and the acetylcholinesterase inhibitor is donepezil or a pharmaceutically acceptable salt thereof, in a dose of 5-23 mg per day.

7. The method of claim 1, wherein each pharmaceutically acceptable salt is a hydrochloride salt.

8. The method of claim 1, wherein the Alzheimer's disease is mild-to-moderate.

9. The method of claim 1, wherein the subject carries two APOE4 alleles.

10. The method of claim 1, wherein the subject carries one APOE4 allele.

11. A method of treating Alzheimer's disease in a subject in need thereof comprising administering to the subject idalopirdine or a pharmaceutically acceptable salt thereof, in a dose of 60-120 mg per day, and an acetylcholinesterase inhibitor or a pharmaceutically acceptable salt thereof, in a dose of 3-24 mg per day; wherein the subject carries one or two APOE4 alleles.

12. The method of claim 11, wherein the acetylcholinesterase inhibitor is selected from the group consisting of donepezil or a pharmaceutically acceptable salt thereof, in a dose of 5-23 mg per day; rivastigmine or a pharmaceutically acceptable salt thereof, in a dose of 3-12 mg per day; and galantamine or a pharmaceutically acceptable salt thereof, in a dose of 8-24 mg per day.

13. The method of claim 12, wherein the acetylcholinesterase inhibitor is donepezil or a pharmaceutically acceptable salt thereof, in a dose of 5-23 mg per day.

14. The method of claim 11, wherein idalopirdine or a pharmaceutically acceptable salt thereof is administered in a dose of 60-90 mg per day.

15. The method of claim 14, wherein idalopirdine or a pharmaceutically acceptable salt thereof is administered in a dose of 60 mg per day.

16. The method of claim 11, wherein idalopirdine or a pharmaceutically acceptable salt thereof is administered in a dose of 60 mg per day; and the acetylcholinesterase inhibitor is donepezil or a pharmaceutically acceptable salt thereof, in a dose of 5-23 mg per day.

17. The method of claim 11, wherein each pharmaceutically acceptable salt is a hydrochloride salt.

18. The method of claim 11, wherein the Alzheimer's disease is mild-to-moderate.

19. The method of claim 11, wherein the subject carries two APOE4 alleles.

20. The method of claim 11, wherein the subject carries one APOE4 allele.

* * * * *